(12) United States Patent
Carter et al.

(10) Patent No.: US 10,036,709 B2
(45) Date of Patent: Jul. 31, 2018

(54) BG METER ILLUMINATED TEST STRIP

(71) Applicant: Roche Diabetes Care, Inc., Indianapolis, IN (US)

(72) Inventors: Robert E. Carter, Pittsboro, IN (US); Matthew C. Sauers, Indianapolis, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 662 days.

(21) Appl. No.: 14/282,364

(22) Filed: May 20, 2014

(65) Prior Publication Data
US 2015/0338349 A1     Nov. 26, 2015

(51) Int. Cl.
| | |
|---|---|
| *G01N 21/77* | (2006.01) |
| *F21V 33/00* | (2006.01) |
| *G01N 33/487* | (2006.01) |
| *A61B 5/15* | (2006.01) |
| *A61B 5/157* | (2006.01) |

(Continued)

(52) U.S. Cl.
CPC .............. *G01N 21/77* (2013.01); *A61B 5/157* (2013.01); *A61B 5/150022* (2013.01); *A61B 5/150358* (2013.01); *F21V 33/0068* (2013.01); *G01N 27/3272* (2013.01); *G01N 27/3273* (2013.01); *G01N 33/48707* (2013.01); *G01N 33/48785* (2013.01); *G01N 33/49* (2013.01);
(Continued)

(58) Field of Classification Search
CPC .................................................. A61B 5/14532
See application file for complete search history.

(56) References Cited

U.S. PATENT DOCUMENTS

| | | | |
|---|---|---|---|
| 4,288,672 A | * | 9/1981 | Puccini .............. H01H 13/7006 200/314 |
| 4,432,366 A | | 2/1984 | Margules |

(Continued)

FOREIGN PATENT DOCUMENTS

| | | |
|---|---|---|
| CN | 1146016 A | 3/1997 |
| DE | 198 19 407 A1 | 11/1998 |

(Continued)

OTHER PUBLICATIONS

DE 198 19 407 A1 Machine Translation.

(Continued)

*Primary Examiner* — Michael C Stout
(74) *Attorney, Agent, or Firm* — Woodard, Emhardt, Moriarty, McNett & Henry, LLP

(57) ABSTRACT

A handheld medical device is configured to illuminate a test strip inserted therein and may include a housing having a port configured to receive a test strip. A circuit board may be mounted inside the housing. A measurement module may be mounted to the circuit board and may be cooperatively operable with the test strip inserted into the port to measure a sample of fluid residing on the test strip. The circuit board faces an opposing top surface of the test strip inserted into the port. A light source may be mounted on the circuit board and operable to emit light substantially perpendicular to the opposing top surface of the test strip inserted into the port. The light source may project the light along an optical axis substantially perpendicular to the opposing top surface of the test strip and illuminate an area surrounding a dosing end of the test strip.

13 Claims, 5 Drawing Sheets

(51) Int. Cl.
*G01N 27/327* (2006.01)
*G01N 33/49* (2006.01)
*F21W 131/20* (2006.01)

(52) U.S. Cl.
CPC .. *A61B 2560/0468* (2013.01); *F21W 2131/20* (2013.01); *Y10T 436/144444* (2015.01)

(56) References Cited

U.S. PATENT DOCUMENTS

| | | | |
|---|---|---|---|
| 5,228,972 | A | 7/1993 | Osaka et al. |
| 5,304,468 | A | 4/1994 | Phillips et al. |
| 5,320,732 | A | 6/1994 | Nankai et al. |
| 5,395,504 | A | 3/1995 | Saurer et al. |
| 5,407,554 | A | 4/1995 | Saurer |
| 5,522,255 | A * | 6/1996 | Neel .............. G01N 11/06 356/39 |
| 5,547,702 | A | 8/1996 | Gleisner |
| 5,563,042 | A | 10/1996 | Phillips et al. |
| 5,651,869 | A | 7/1997 | Yoshioka et al. |
| 5,686,829 | A | 11/1997 | Girault |
| 5,997,817 | A | 12/1999 | Crismore et al. |
| 6,201,607 | B1 | 3/2001 | Roth et al. |
| 6,514,460 | B1 | 2/2003 | Fendrock |
| 6,830,551 | B1 | 12/2004 | Uchigaki et al. |
| 6,847,451 | B2 | 1/2005 | Pugh |
| 7,276,027 | B2 | 10/2007 | Haar et al. |
| 7,285,198 | B2 | 10/2007 | Douglas |
| 7,867,369 | B2 * | 1/2011 | Bhullar .............. G01N 27/3272 204/403.01 |
| 7,991,257 | B1 * | 8/2011 | Coleman ............ B29D 11/0073 264/1.24 |
| 8,431,408 | B2 * | 4/2013 | Lewis ................ A61B 5/14532 422/401 |
| 8,465,977 | B2 | 6/2013 | Joseph et al. |
| 2003/0161572 | A1 * | 8/2003 | Johnck .............. B01L 3/502707 385/14 |
| 2003/0207441 | A1 | 11/2003 | Eyster et al. |
| 2003/0211636 | A1 * | 11/2003 | Bedian ................ C07K 16/44 436/518 |
| 2004/0032748 | A1 * | 2/2004 | Trudeau ............. B28B 23/0037 362/554 |
| 2004/0219691 | A1 | 11/2004 | Shartle et al. |
| 2005/0009126 | A1 | 1/2005 | Andrews et al. |
| 2005/0023137 | A1 | 2/2005 | Bhullar et al. |
| 2005/0201897 | A1 | 9/2005 | Zimmer et al. |
| 2005/0265094 | A1 | 12/2005 | Harding et al. |
| 2005/0276133 | A1 | 12/2005 | Harding et al. |
| 2006/0099108 | A1 | 5/2006 | List et al. |
| 2006/0100542 | A9 | 5/2006 | Wong et al. |
| 2006/0222567 | A1 | 10/2006 | Kloepfer et al. |
| 2007/0167869 | A1 * | 7/2007 | Roe .................... A61B 5/14532 600/583 |
| 2007/0255301 | A1 | 11/2007 | Freeman et al. |
| 2010/0021342 | A1 * | 1/2010 | Joseph ............. G01N 33/48785 422/400 |
| 2010/0208488 | A1 * | 8/2010 | Luo ...................... F21V 7/0091 362/555 |
| 2011/0149591 | A1 * | 6/2011 | Smith .................. A61B 3/0008 362/555 |
| 2012/0095316 | A1 * | 4/2012 | Lewis ................ A61B 5/14532 600/365 |
| 2013/0105074 | A1 * | 5/2013 | Riggles ............. B01L 3/502707 156/269 |
| 2013/0146478 | A1 * | 6/2013 | Iyengar .............. G01N 21/7703 205/775 |
| 2014/0078772 | A1 * | 3/2014 | Gaydoul ................ G02B 6/001 362/555 |
| 2014/0268864 | A1 * | 9/2014 | Lee ...................... G02B 6/0085 362/558 |

FOREIGN PATENT DOCUMENTS

| | | | |
|---|---|---|---|
| DE | 198 49 539 A1 | 5/2000 | |
| DE | 198 57 426 A1 | 6/2000 | |
| DE | 101 05 549 A1 | 8/2002 | |
| EP | 0 407 800 A2 | 1/1991 | |
| EP | 1 199 978 B1 | 5/2002 | |
| EP | 1 424 040 A1 | 6/2004 | |
| EP | 1 918 707 A2 | 5/2008 | |
| EP | 2 377 465 A1 | 10/2011 | |
| JP | 05-164756 A | 6/1993 | |
| KR | 816799 B1 | 3/2008 | |
| WO | WO 9216909 A1 * | 10/1992 | ......... G06K 7/10722 |
| WO | WO 2001/08551 A2 | 2/2001 | |
| WO | WO 2005/119234 A2 | 12/2005 | |
| WO | WO-2005119234 A2 | 12/2005 | |
| WO | WO 2012003306 A1 * | 1/2012 | ........... G01N 27/327 |

OTHER PUBLICATIONS

DE 198 49 539 A1 Machine Translation.
DE 198 57 426 A1 Machine Translation.
European Patent Application No. 09 777 286.7 Office Action dated Jul. 14, 2011.
Glucometer Elite® Diabetes Care System User Guide, Bayer Corporation, Elkhart, IN, Rev. 6/98.
International Application No. PCT/EP2009/005233 International Preliminary Report on Patentability dated Oct. 8, 2010.
International Application No. PCT/EP2009/005233 International Search Report and Written Opinion dated Oct. 22, 2010.
International Patent Application No. PCT/EP03/13298 International Search Report dated Apr. 10, 2004.
JP 05-164756 A English Language Abstract.
U.S. Appl. No. 10/008,788, "Fourth Supplemental Information Disclosure Statement", dated Mar. 8, 2007.

* cited by examiner

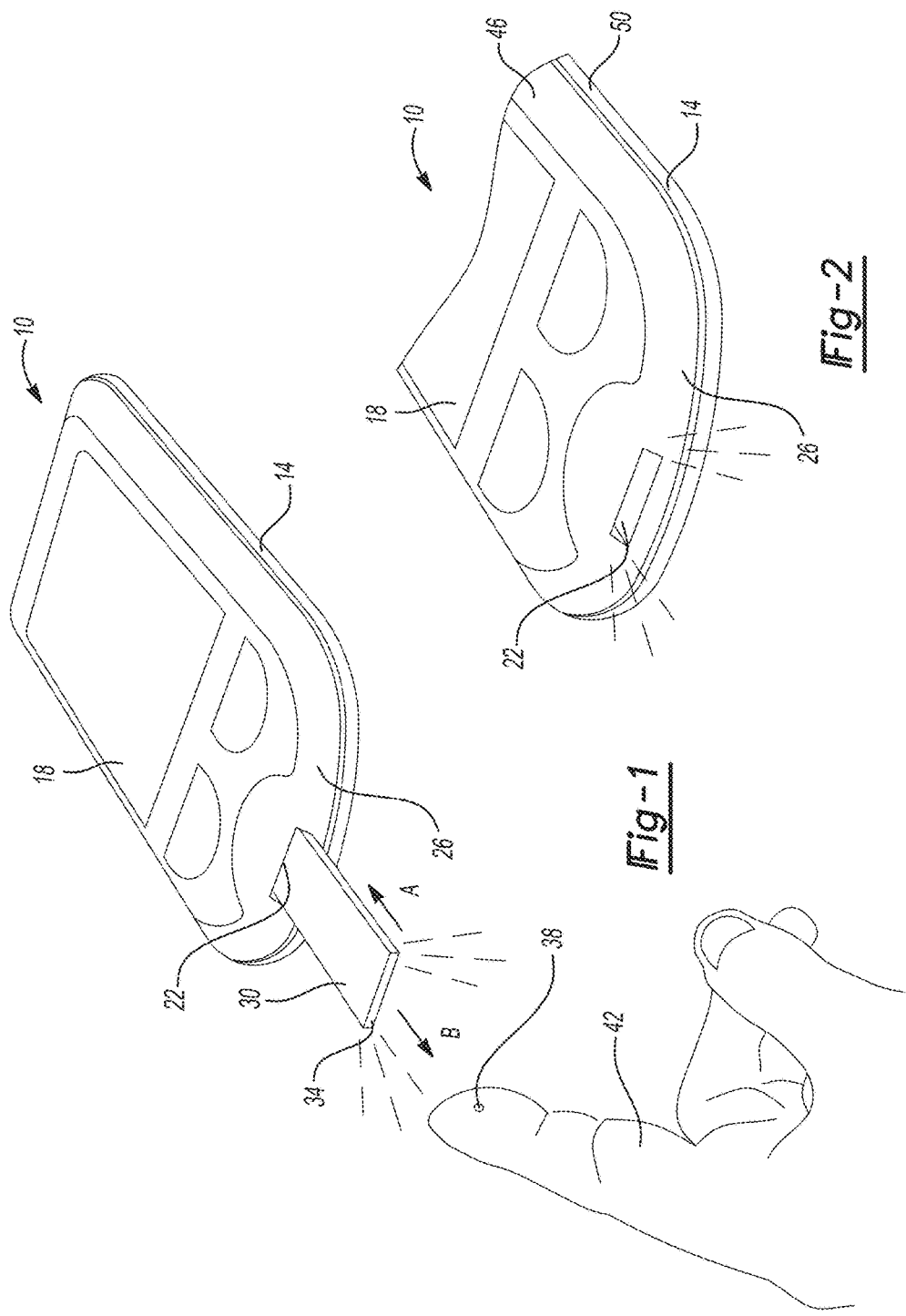

BG METER ILLUMINATED TEST STRIP

FIELD

The present disclosure relates to a handheld diabetes managing device and, more particularly, relates to a handheld diabetes managing device with a light system for enhanced illumination of a test strip and an area proximate to the test strip.

BACKGROUND

Diabetes mellitus, often referred to as diabetes, is a chronic condition in which a person has elevated blood glucose levels that result from defects in the body's ability to produce and/or use insulin. Diabetes is managed primarily by determining and controlling the level of glucose in the bloodstream.

Blood glucose diagnostic information is typically obtained from a capillary blood sample with a lancing device and is then measured with a handheld blood glucose meter. There are times in which the diabetes patient may wish to perform personal glucose testing in low light conditions. For instance, the patient may want to perform the test in a dark or poorly lit room. Because the test requires a certain amount of precision (e.g., proper placement of a blood droplet on the dosing area of a test strip), it can be difficult to complete the test in such conditions. Known handheld diabetes management devices providing illumination in such situations are not capable of providing all of the capabilities of illuminating the insertion location of a test strip, and a dosing location on the test strip.

Further, known handheld diabetes management devices are limited in areas that can support a light source for such illumination. Often light must be directed through an interior of the handheld diabetes management device in a light pipe before illuminating the test strip. The light pipe adds size, weight and cost to the device.

This section provides background information related to the present disclosure which is not necessarily prior art.

SUMMARY

This section provides a general summary of the disclosure, and is not a comprehensive disclosure of its full scope or all of its features.

A handheld diabetes management device for providing enhanced illumination on a dosing area of a diabetes test element is disclosed. The diabetes management device includes a housing receiving a test strip through a port in the housing. A circuit board is mounted inside the housing and faces an opposing top surface of the test strip. A measurement module is mounted to the circuit board and is cooperatively operable with the test strip inserted into the port to measure a sample of fluid residing on the test strip. A light source is mounted on the circuit board and is operable to emit light substantially perpendicular to the opposing top surface of the test strip. The light source projects the light along an optical axis substantially perpendicular to the opposing top surface of the test strip and illuminates an area surrounding a dosing end of the test strip.

According to other aspects, a handheld diabetes management device includes a housing. A strip connector is positioned within the housing and is configured to receive a test element. A circuit board having a first side and a second side is mounted inside the housing. A measurement module is positioned proximate to the strip connector and is mounted to the first side. A light source is mounted on the first side and is operable to emit photons substantially perpendicular to the top surface of the test element. A first layer of the test element receives and transmits the photons along a length of the test element, discharging the photons at a dosing area.

Moreover, a method of providing test strip illumination is disclosed. The method includes slitting a sheet of material to form first and second ends of a test strip, such that a light path is not altered when passed through the first or second end; cutting the slit portions of material to form first and second sides of the test strip, such that the sides include micro serrations; passing a light beam through a top side of the test strip at an optical axis perpendicular the top side; and transmitting the light beam through the test strip to illuminate an area surrounding a dosing area of the test strip, wherein the first and second ends create a constructive interference of the light beam in a length-wise direction and the first and second sides create a destructive interference of the light beam in a width-wise direction, channeling the light beam through a center of the test strip and toward the dosing area.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 1 is a perspective view of a handheld diabetes managing device according to the present disclosure;

FIG. 2 is a perspective view of the handheld diabetes managing device of FIG. 1 depicting light exiting a strip port when a test strip is not present;

Corresponding reference numerals indicate corresponding parts throughout the several views of the drawings.

DETAILED DESCRIPTION

Figure 3:
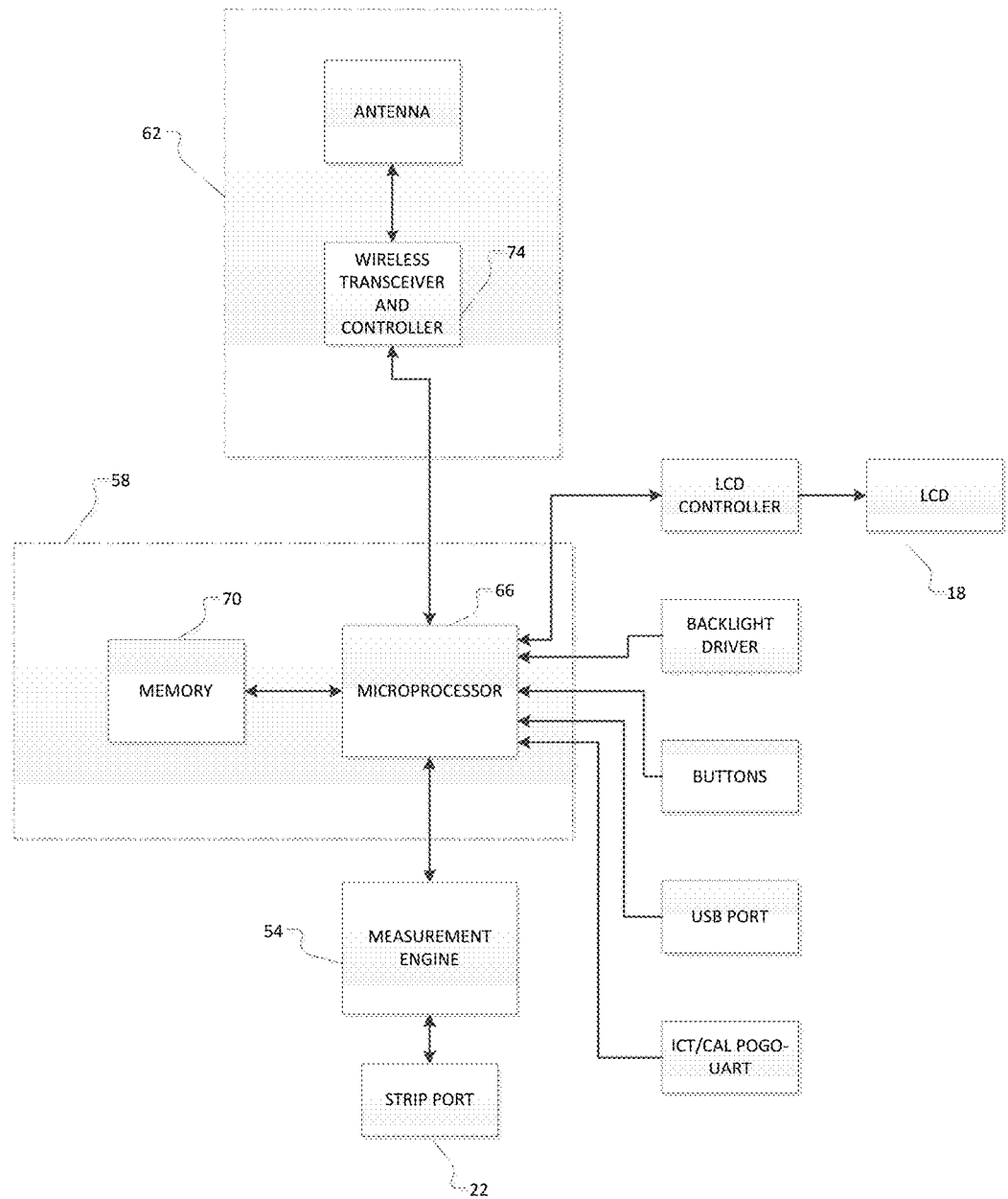
FIG. 3 is a block diagram of an exemplary hardware arrangement for the handheld diabetes managing device of FIG. 1.

Example embodiments will now be described more fully with reference to the accompanying drawings.

Referring initially to FIGS. 1 and 2, an example embodiment of a portable, handheld diabetes management device 10 is illustrated according to the present teachings. Diabetes management device 10 includes a housing 14 sized to fit in a hand of a user, and includes a view port or screen 18 which provides digital test results and provides for user input. An access port, or strip port, 22 positioned at a body end 26, slidably receives a test strip, or test element, 30, which is discussed in further detail below. Test strip 30 is slidably inserted in access port 22 in an insertion direction "A" for testing, and is slidably removed in an opposite removal direction "B" at the conclusion of testing. Device 10 provides an internal light source which is capable of illuminating test strip 30. With test strip 30 in a test position, light is emitted from a perimeter edge/dosing area 34 such that a dose/sample 38 of a bodily fluid from a user 42, such as on the user's finger, is illuminated, as well as a general area proximate to body end 26 of housing 14.

Device 10 may be used for analyzing a body fluid disposed on edge/dosing area 34. For instance, as will be discussed, test strip 30 can be a disposable glucose test strip of the type discussed below. In the example embodiment, a droplet of blood is applied from dose/sample 38 while test strip 30 is inserted within device 10, and device 10 analyzes the droplet to detect a blood glucose level therein. In an alternative embodiment, the body fluid is applied from dose/sample 38 while test strip 30 is removed from device 10 and then inserted into device 10 for analysis. It will be appreciated that while device 10 analyzes blood in the example embodiment, in alternative embodiments, device 10 could be used for analyzing any other suitable characteristic of any other body fluid without departing from the scope of the present disclosure.

Referring specifically to FIG. 2, device 10 can include first and second portions 46, 50 of housing 14. First and second portions 46, 50 can be removably coupled together such that first and second portions 46, 50 define an interior space there-between, which is used to house various components therein, as will be discussed below. When test strip 30 is not positioned in access port 22, light generated from within housing 14 is emitted through access port 22 to illuminate the area about body end 26, which also is effective in low light areas to assist the user in aligning test strip 30 and/or to improve visibility of the area at dose/sample 38. In the example embodiment, access port 22 is a through-hole with an ovate or rectangular shape extending through body end 26 of first portion 46 of housing 14. However, in other embodiments, access port 22 may be a through-hole with an ovate or rectangular shape extending through second portion 50.

FIG. 3 depicts an exemplary hardware arrangement for device 10. Device 10 is comprised generally of a measurement engine 54, a processing subsystem 58 and a communication subsystem 62. Each of these components is further described herein. While the primary components are discussed herein, it is understood that other components (e.g., batteries or a power source) may be needed for the overall operation of device 10.

Measurement engine 54 cooperatively interacts with test strip 30 inserted into access port 22 to determine the glucose measure from sample 38 on test strip 30. Measurement engine 54 may include calibration information for test strips 30 being read by device 10. Measurement engine 54 may refer to, be part of, or include, an application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above. Measurement engine 54 may further include memory that stores code executed by the processor, where code, as used above, may include software, firmware, and/or microcode, and may refer to programs, routines, functions, classes, and/or objects.

Processing subsystem 58 is configured to receive the glucose measures from measurement engine 54 which may in turn be stored in memory by processing subsystem 58. Glucose measures may also be displayed by processing subsystem 58 on display 18. The user can interact with device 10 using various user interface components, such as buttons, switches, a speaker, a microphone, USB port, etc. Each of these components is interfaced with processing subsystem 58. In an exemplary embodiment, processing subsystem 58 includes a microprocessor 66 and one or more volatile and/or non-volatile memories 70, although other implementations are envisioned for the processing subsystem.

Processing subsystem 58 is also interfaced with communication subsystem 62. In an exemplary embodiment, communication subsystem 62 includes a wireless transceiver 74. Wireless transceiver 74 operates to communicate the glucose measures and other data wirelessly via a data link to a remote device physically separated from device 10. Communication subsystem 62 can also include an antenna, microcontroller, voltage and power control circuits and a flash memory device. Although a few primary components of device 10 are discussed herein, it is readily understood that other components (e.g., a power source) may be needed to implement device 10.

Figure 4:
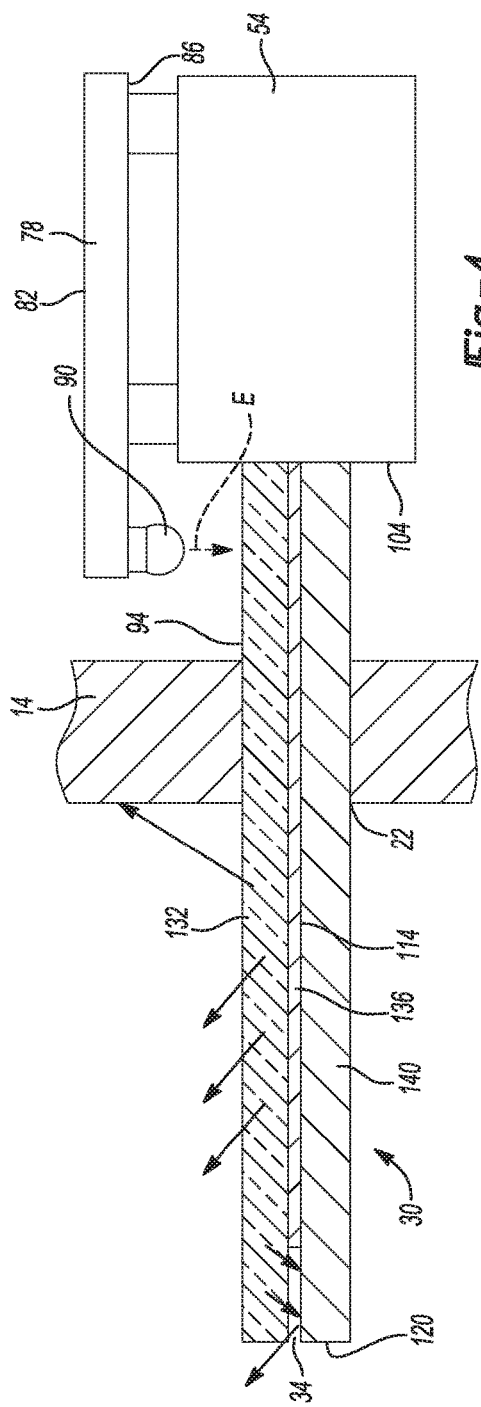
FIG. 4 is a side perspective view of the interior components of the handheld diabetes managing device of FIG. 1.

Referring now to FIG. 4, device 10 may further include a circuit board 78 having a top side 82 and a bottom side 86. In the example embodiment, circuit board 78 may be a printed circuit board with various circuits and circuit components included thereon. Measurement engine 54 or other components from the processing subsystem 58 may be included on circuit board 78 and may control the internal components.

In the example embodiment, a light source 90 is mounted to circuit board 78. Light source 90 can be of any suitable type, such as a light emitting diode (LED). Light source 90 is mounted to the same side of circuit board 78 as the measurement engine 54 (i.e., bottom side 86 of circuit board 78). In an alternative embodiment, light source 90 may be mounted to top side 82 of circuit board 78. In still another embodiment, light source 90 may be mounted separate from circuit board 78 and connected to circuit board 78.

In the example embodiment, light source 90 is positioned approximately 0.0001 and 0.001 inches from a first surface 94 of test strip 30 when test strip 30 is in the testing position. The closer light source 90 is positioned to first surface 94, the better the transmission of light through test strip 30. In alternative embodiments, light source 90 may be in contact with first surface 94. Since light source 90 is positioned to emit light directly on to test strip 30, no alignment of light source 90 with respect to test strip 30 is necessary. Further, there is no need for additional apparatuses to direct light to a location on test strip 30.

Measurement engine 54 can be of a known type for analyzing body fluid applied to test strip 30 as discussed above. Measurement engine 54 can be operably mounted to circuit board 78 and can communicate with access port 22. As such, when test strip 30 is inserted within access port 22 and body fluid is applied, measurement engine 54 can perform the predetermined analysis. Moreover, measurement engine 54 may include associated software and logic for performing and controlling the analysis of the body fluid.

Figure 5:
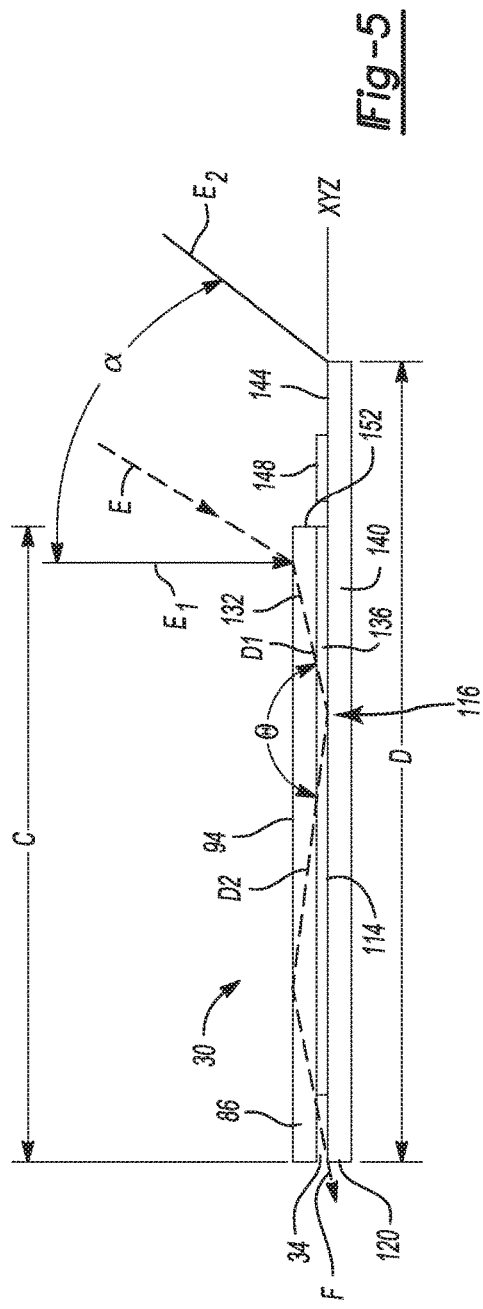
FIG. 5 is a side view of a test strip according to the present disclosure.
Figure 6:
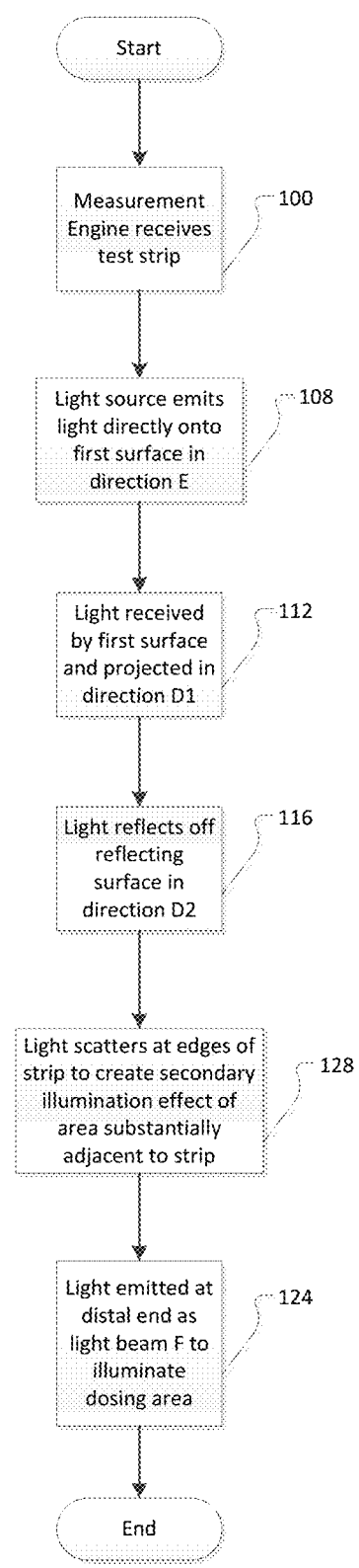
FIG. 6 is a flow chart illustrating a method for illuminating a dosing area of a test strip.

During operation, as shown in FIG. 6 with additional reference to FIGS. 4 and 5, at 100, test strip 30 is received within measurement engine 54 and abuts an exterior wall 104 of measurement engine 54. At 108, light from light source 90 is emitted toward test strip 30 in a direction E which is oriented within a range of incident rays E1 to E2 defining an angular range alpha ($\alpha$) from zero degrees or normal to approximately 45 degrees measured with respect to incident ray E1. In the example embodiment of FIG. 3, direction E is substantially perpendicular (for example, within 5 degrees of perpendicular) to first surface 94, such that the light is emitted directly onto first surface 94 of test strip 30. In alternative embodiments, light source 90 may emit light at an angle between zero and forty degrees from the perpendicular towards dosing area 34. By emitting the light at an angle, the efficiency of the light transmission through the strip may be improved; however, the mounting angle of light source 90 may need to be modified.

At 112, first surface 94 receives the light traveling in direction E. In some embodiments, first surface 94 may scatter the light from the original light beam. In other embodiments, first surface 94 may alter the part of the light from direction E. Test strip 30 receives the light and transmits the light in a first direction D1 toward a reflecting surface 114. At 116, the light reflects from the reflecting surface 120 and is redirected toward a second direction D2 (shown in FIG. 5). The second direction D2 may be at a nonzero angle θ relative to the first direction D1. For the example embodiment, the angle θ may be approximately ninety degrees (90°). In other embodiments, the angle θ may be greater than or less than ninety degrees (90°) depending on reflection properties of the material. Once the light is redirected toward the second direction D2, the light reflects between reflecting surface 114 and first surface 94, traveling along a longitudinal axis XYZ through test strip 30 and out a distal end 120 of test strip 30. Thus test strip 30 efficiently transmits the light generated by light source 90 out of housing 14, through test strip 30, to illuminate dosing area 34. The light will exit as emitted light rays F. As such, the user more easily recognizes where to apply a blood droplet for glucose analysis, and proper application of the blood droplet to dosing area 34 is more likely. In the example embodiment, at 128, while the light is transmitted through test strip 30 to illuminate dosing area 34, the light is emitted through first surface 94 in a light scattering pattern to create a secondary illumination effect of an area substantially adjacent to test strip 30. However, in alternative embodiments, the light may remain within the test strip 30 and exit only at dosing area 34.

Referring specifically to FIG. 5, in the example embodiment test strip 30 may be a multiple layer strip having at least a longitudinal transparent layer 132 defining a first layer which is applied onto a second layer 136. Second layer 136 is further applied to a third layer 140. Longitudinal transparent layer 132 has a length "C" which is greater than a length of second layer 136 and less than a length "D" of third layer 140, such that a recess at dosing area 34 is created on distal end 120 for receiving dose/sample 38. Further, a free surface 144 having electrical contacts 148 extends beyond an end 152 of longitudinal transparent layer 132. Free surface 144 and electrical contacts 148 are received within measurement engine 54 such that end 152 of longitudinal transparent layer 132 and second layer 136 abuts measurement engine 54.

Longitudinal transparent layer 132 is a clear, transparent, or translucent, layer and may be of any material that is clear or transparent. For example, first layer 132 may be a polyethylene layer, a glass layer, or any other material. First layer 132 may also have low reflectivity. In some embodiments, second layer 136 may be of a similar material and may act as a spacer between first layer 132 and third layer 140. In alternative embodiments, second layer 136 may be an adhesive for securing first layer 132 to third layer 140. Further, in still other embodiments, second layer 136 may include a reagent. Third layer 140 may contain a metal for electrodes and a reagent. In the example embodiment, at least one of second layer 136 and third layer 140 must be of an opaque material. The at least one layer of the opaque material may also be reflective to guide the light beam through test strip 30.

Figure 7:
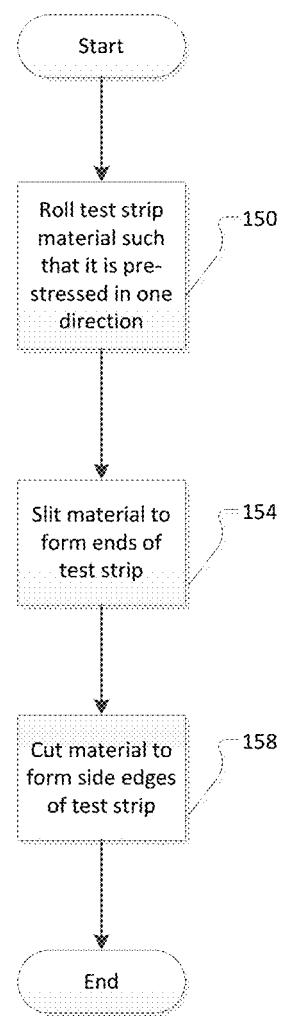
FIG. 7 is a flow chart illustrating a method for manufacturing a test strip.

Now referring to FIG. 7, test strips 30 are manufactured such that the light beam travels in a lambertian distribution (i.e., a three-dimensional bell curve) across the width of test strip 30, through the length of test strip 30. At 150, test strips 30 are formed from a rolled piece of material that is pre-stressed in one direction. A transmission angle is different in different directions, which somewhat polarizes longitudinal transparent layer 132. At 154, the rolled piece of material is slit across a width and along a length of a web forming ends perpendicular to first surface 94 of test strip 30. The ends of each test strip are smooth and contain no striations to alter light paths through them. For example, the material is drawn across a blade, such that the material is parted and separated instead of sawing or removing material. The resulting cut creates constructive interference in the lengthwise direction of test strip 30. At 158, the slit pieces of material are cut forming edges perpendicular to first surface 94 of test strip 30. The edges include micro serrations left on the cut edge providing for a rough edge on each side of test strip 30. For example, the material is cut by a vertical knife edge whose travel is perpendicular to a plane of test strip 30, thus leaving a plurality of vertical striations similar to a lenticular lens and dulling the emitted light from the side surfaces of test strip 30. The resulting cut creates destructive interference in the width-wise direction.

While, in the example embodiment, longitudinal transparent layer 132 is described as being a clear transparent layer, in alternative embodiments, longitudinal transparent layer 132 could also include a polarizing film. When the longitudinal transparent layer 132 is polarized, the light is not dispersed within the layer, but, instead, travels in a more columnized form through the length of test strip 30, resulting in less light being dispersed along test strip 30 and more light exiting as light beam F." Further, in an alternative embodiment, dosing area 34 of test strip 30 may be of a light scattering texture to disperse the light beam.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A medical device comprising:
    a housing having a strip port configured to receive a test strip therein;
    a test strip configured to be received within the strip port, the test strip having a first end received within said housing and a second end extending outside of said housing, said test strip including a top polarized layer positioned over a separate bottom layer, said test strip further including a transparent or translucent intermediate spacer layer sandwiched between the top layer and the bottom layer, the top layer being transparent or translucent and defining a first surface facing away from the bottom layer and the bottom layer defining a second surface facing toward the top layer; and a light source within the housing operable to emit light directly onto the first surface of the top layer, the first surface being adapted to allow passage of light emitted by said light source to pass through the first surface and into the top layer, the second surface being adapted to reflect light received from the top layer, the light, directed by said light source onto the top layer passing through the first surface and being directed by the top layer toward the second surface and in a direction from the first end to the second end, the light directed toward the second surface being reflected off the second surface, light reflected from the second surface to the first surface being reflected off the first surface, light emitted by said light source exiting from the test strip adjacent to the second end.

2. A medical device comprising:

a housing having a strip port configured to receive a test strip therein;

a test strip configured to be received within the strip port, the test strip having a first end received within said housing and a second end extending outside of said housing, said test strip including a top polarized layer positioned over a separate bottom layer, said test strip further including a transparent or translucent intermediate spacer layer sandwiched between the top layer and the bottom layer, the top layer being transparent or translucent and defining a first surface facing away from the bottom layer and the bottom layer defining a second surface facing toward the top layer, to spacer layer including a third surface positioned adjacent and forming an interface with the second surface of the bottom layer; and a light source within the housing operable to emit light directly onto the first surface of the top layer, the first surface being adapted to allow passage of light emitted by said light source to pass through the first surface and into the top layer, the interface being adapted to reflect light received from the top layer, the light directed by said light source onto the top layer passing through the first surface and being directed by the top layer toward the interface and in a direction from the first end to the second end, the light directed toward the interface being reflected off the interface, light reflected from the interface to the first surface being reflected off the first surface, light emitted by said light source exiting from the test strip adjacent to the second end.

3. A medical device comprising:

a housing having a strip port configured to receive a test strip therein;

a test strip configured to be received within the strip port the test strip having a first end received within said housing and a second end extending outside of said housing, said test strip including a bottom layer having an upper surface, a spacer layer comprising a transparent or translucent material and having a bottom surface received against the upper surface, of the bottom layer, the spacer layer further having an upper surface, and a top layer comprising, a transparent or translucent material and having a bottom surface received against the upper surface of the spacer layer, the top layer further having an upper surface, the spacer layer including an opening at the second end defining a test chamber between the upper surface of the bottom layer and the bottom surface of the top layer; and a light source within said housing operable to emit light directly onto the upper surface of the top layer, the upper surface of the top layer being adapted to provide passage of light emitted by said light source through the top layer and into the spacer layer, and the upper surface of the top layer being adapted to reflect light received from the spacer layer, the spacer layer being adapted to provide passage of light received from the top layer through the spacer layer and reflected back at the bottom of the spacer layer, light emitted by said light source passing through both of the top and spacer layers and exiting the test strip adjacent to the second end.

4. The medical device of claim 3 in which said light source is operable to emit light against the first surface at an incidence angle from 0° to 45° from normal to the first surface.

5. The medical device of claim 3 in which said light source is operable to emit light against the first surface at an incidence angle of less than 5° from normal to the first surface.

6. The medical device of claim 3 in which the bottom layer is opaque.

7. The medical device of claim 3 in which the top layer is a polarized layer.

8. The medical device of claim 3 in which the first and second layers include side edges perpendicular to the first surface having micro serrations providing destructive interference in the widthwise direction.

9. The medical device of claim 3 in which the top layer is longer than the spacer layer, and the top layer is shorter than the bottom layer.

10. The medical device of claim 9 in which the top layer and bottom layer have first and second ends, the second ends extending beyond the spacer layer to form a test chamber therebetween.

11. The medical device of claim 10 in which the first end of the bottom layer extends beyond the spacer layer and includes electrical contacts.

12. The medical device of claim 10 and which further includes a measurement engine in said housing, the bottom layer being received in said housing abutting said measurement engine.

13. The medical device of claim 3 in which the spacer layer and the top layer both extend both inside and outside said housing.

* * * * *